United States Patent [19]

Olsen

[11] Patent Number: 4,541,802
[45] Date of Patent: Sep. 17, 1985

[54] SWIVEL HOSE COUPLING FOR DENTAL HANDPIECE OR THE LIKE

[75] Inventor: Robert A. Olsen, Palatine, Ill.

[73] Assignee: Sybron Corporation, Rochester, N.Y.

[21] Appl. No.: 686,117

[22] Filed: Dec. 24, 1984

[51] Int. Cl.[4] .............................................. A61C 1/08
[52] U.S. Cl. ..................................... 433/126; 433/29
[58] Field of Search .................................. 433/126, 29

[56] References Cited

U.S. PATENT DOCUMENTS

| 4,213,243 | 7/1980 | Flatland | 433/126 |
| 4,260,382 | 4/1981 | Thomson | 433/126 |
| 4,398,885 | 8/1983 | Loge et al. | 433/29 |
| 4,403,956 | 9/1983 | Nakanishi | 433/29 |
| 4,403,957 | 9/1983 | Mossle et al. | 433/29 |
| 4,431,412 | 2/1984 | Lares et al. | 433/29 |

Primary Examiner—John J. Wilson
Attorney, Agent, or Firm—Robert A. Gerlach; Robert J. Bird

[57] ABSTRACT

A swivel coupling for connecting a hose containing a drive air conduit, a secondary air conduit, a water conduit and an optical fiber conduit to a handpiece, such as a dental handpiece, having like conduits. The coupling permits unlimited swiveling, and efficient use of space by means of concentric annular passages in a central swivel tube.

2 Claims, 3 Drawing Figures

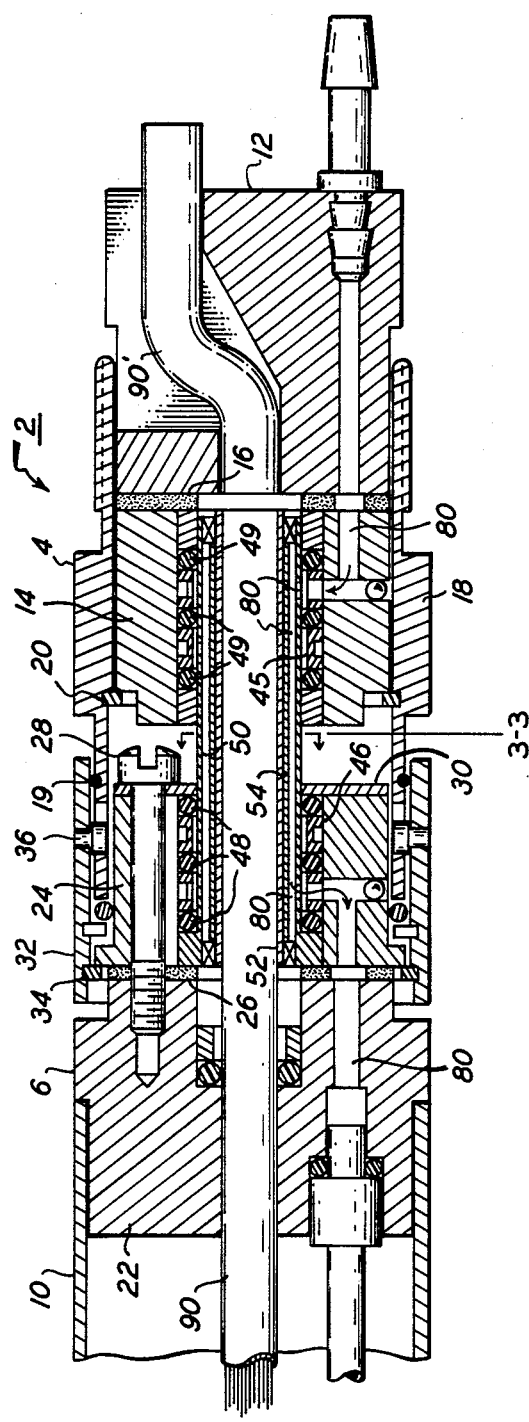
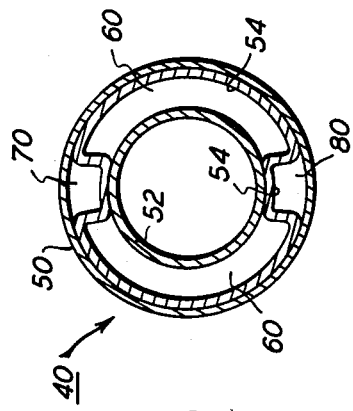
FIG. 1
FIG. 3

SWIVEL HOSE COUPLING FOR DENTAL HANDPIECE OR THE LIKE

BACKGROUND AND SUMMARY OF THE INVENTION

The subject matter of this invention is a swivel coupling for connecting a hose containing a plurality of conduits to a handpiece such as a dental handpiece having like conduits. More specifically, the swivel coupling of this invention connects a hose containing conduits for drive air, secondary air, water, and light to a dental handpiece having like conduits for drive air to drive a turbine motor, secondary air or chip air for scavenging a work area, water for washing and cooling the work area, and optical fibers for illuminating the work area.

The most relevant prior art I know of is U.S. Pat. No. 4,431,412 issued Feb. 14, 1984 to Joseph and Albert Lares. The Lares patent discloses a dental handpiece with swivel coupling for transmitting air, water and light. As will be readily appreciated from FIGS. 3-6 of the Lares patent, the several passages for drive air, secondary air, water and light are arranged in discrete, non-contiguous positions within a cylindrical spool member. The light conductor passes through the center passage and the other passages are arranged around it, exiting the spool radially at points spaced longitudinally along it.

The present invention makes more efficient use of space within the swivel coupling.

The present invention may be summarized as a swivel coupling for transmitting drive air, secondary air, water and light. A hose containing separate conduits for all these media is threaded to one end of the coupling, a handpiece having like conduits is threaded to the other end, and the two ends or halves of the coupling are rotatably connected to each other. Within the coupling is a spool or cartridge including an outer casing and a concentric inner tube for an optical fiber bundle, the space between casing tube defining arcuate passages for drive air, secondary air, and water. These several passages communicate with corresponding passages in the handpiece and in the hose end of the coupling for unlimited swivel capability.

DRAWING

FIG. 1 is a sectional view of a swivel coupling according to this invention.

FIG. 3 is an axial section taken along the line III—III of FIG. 1 and enlarged to show detail.

DESCRIPTION

Figure 2:
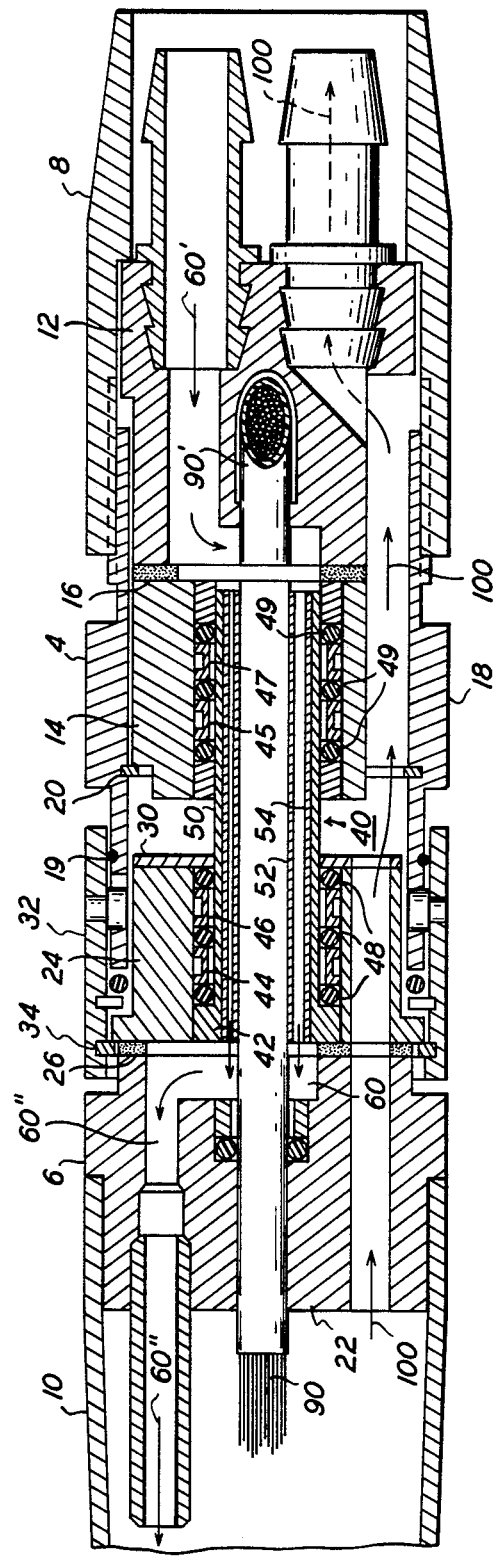
FIG. 2 is a sectional view of the same device, rotated 90° from its FIG. 1 orientation.

With reference to the drawing, the swivel coupling of this invention is generally indicated at 2 and includes a hose connector portion 4 and a handpiece connector portion 6. The hose connector portion 4 of the coupling is adapted for threaded sealing connection, by means of supply hose fitting 8, to a supply hose (not shown) which includes conduits for drive air, exhaust air, secondary or chip air, water, and light. The handpiece connector portion 6 of the coupling is adapted for threaded sealing connection to a dental handpiece 10 which also includes conduits for drive air, exhaust air, chip air, and light. The various conduits in the supply hose are in registry with corresponding conduits in the hose connector portion 4 of the coupling, and the conduits in the handpiece 10 are in registry with corresponding conduits in the handpiece connector portion 6 of the coupling. The details of the hose and handpiece connections are not material to the present invention.

The hose connector portion 4 of the swivel coupling 2 includes a hose adaptor 12 and a ported spool member 14 with a sealing gasket 16 between them. A hose connector ring 18 surrounds adaptor 12 and spool member 14 and is threaded for connection to hose fitting 8 which abuts against a shoulder on the adaptor 12 to effect a tight sealing engagement of hose fitting 8 against adaptor 12 and spool member 14. Connector ring 18 secures this compression by means of an internal snap ring 20 which bears against the spool member 14. Connector ring 18 also includes an external sealing O-ring 19.

The handpiece connector portion 6 of the swivel coupling 2 includes a handpiece adaptor 22 and a ported spool member 24 with a gasket 26 between them. Spool 24, gasket 26, and adaptor 22 are firmly held together by one or more cap screws 28 bearing against an annular retaining ring 30, spool member 24 and gasket 26, and threaded into the handpiece adaptor 22. A disconnect ring 32 is rotatably mounted on the adaptor 22 - spool 24 by means of a snap ring 34. Disconnect ring 32 and hose connector ring 18 are adapted for connection by a bayonet fitting 36, and when so connected the O-ring 19 seals the radial clearance between them.

When the coupling 2 is connected as just described, the handpiece portion 6 (with adaptor 22 and spool 24) is rotatable or swivelable relative to the hose portion 4 (with disconnect ring 32, hose connector ring 18, spool 14, and hose adaptor 12).

A swivel tube 40, including a circumferential flange 42, is mounted to the handpiece adaptor 22 and is held in place by retaining ring 30 acting against flange 42 through a pair of spacer rings 44 and 46 which are separated and sealed by O-rings 48 in compression. Swivel tube 40 extends into spool member 14 in the hose portion of the coupling 2 and is surrounded, within spool 14, by a pair of spacer rings 45 and 47 which are separated and sealed by O-rings 49 in compression.

Swivel tube 40 is shown in enlarged axial cross-section in FIG. 3 and includes an outer cylindrical casing 50, an inner concentric cylindrical casing 52, and a spacer member 54 separating the inner and outer casings 50, 52 and defining longitudinal passages 60 for drive air, 70 for chip air, and 80 for water. An optical fiber bundle 90 extends through the inner casing 52, through the handpiece adaptor 22, and on into the body of handpiece 10. Fiber bundle 90 is in registry with a corresponding fiber bundle 90' in the hose adaptor 12, from which it receives light.

Drive air passage 60 in the swivel tube 40 is open at each end and communicates through gasket 16 with drive air passage 60' in the hose adaptor 12, and through gasket 26 with drive air passage 60" in the handpiece adaptor 22.

The sectional view of FIG. 1 shows the flow path of water through the coupling. The water passage 80 extends through the hose adaptor 12 and spool member 14, into the annular space defined by spacer ring 47, thence through a radial port in the outer casing 50 and into the swivel tube water channel defined by spacer 54. At the handpiece end of swivel tube 40, water passage 80 extends through another radial port in outer casing 50 into the annular space defined by spacer ring 44, thence into spool member 24, handpiece adaptor 22, and into the handpiece. A similar flow path 70 for chip air extends through hose adaptor 12, spool member 14 and into the annular space defined by spacer ring 45, through a radial port in the outer casing 50 and into the swivel tube chip air channel defined by spacer 54. At the handpiece end of swivel tube 40, air passage 70 proceeds out through a radial port in casing 50, through the annular space defined by spacer ring 46, into spool member 24, handpiece adaptor 22 and into the handpiece. Much of the chip air path 70 does not appear in the sectional views of FIGS. 1 and 2, but it is substantially identical or parallel to the water path 80.

Exhaust air from the handpiece turbine flows along a path 100 from the handpiece, through handpiece adaptor 22, through spool members 24 and 14, hose adaptor 12 and finally into the hose.

As will be appreciated from FIG. 3, the swivel tube 40 with its inner and outer casings 50 and 52 and the spacer member 54 provides a much greater proportion of its cross-sectional area for fluid flow than does the prior art. In addition, the flow passages are relatively simpler and more economical to manufacture than the drilled passages of the prior art.

What is claimed is:

1. A swivel coupling for connecting a hose containing a plurality of fluid conduits and an optical fiber light conduit to a handpiece having corresponding conduits,
   said coupling having a hose connector portion for connection to said hose and a handpiece connector portion for connection to said handpiece, said hose connector portion and said handpiece connector portion of said coupling being in sealed rotatable engagement with each other,
   a swivel tube mounted to said handpiece connector portion and adapted for mating sealing engagement within said hose connector portion, said swivel tube including an outer cylindrical casing, an inner concentric cylindrical casing, and a spacer member separating said inner and outer casings and defining therewith a plurality of longitudinal passages,
   said inner casing containing an optical fiber light guide in optical communication with the light conduit in said hose,
   said plurality of passages in said swivel tube communicating with corresponding conduits in said hose connector portion and said handpiece connector portion,
   whereby said swivel coupling provides for the transmission therethrough of drive air, secondary air, water and light with unlimited swivel capability and with maximum use of space within said swivel tube.

2. A swivel coupling for connecting a hose containing a drive air conduit, a secondary air conduit, a water conduit, and an optical fiber light conduit, to a handpiece having a drive air conduit, a secondary air conduit, a water conduit, and an optical fiber light conduit,
   said coupling having a hose connector portion adapted for threaded sealing engagement with said hose and a handpiece connector portion adapted for threaded sealing engagement with said handpiece, said hose connector portion and said handpiece connector portion of said coupling being in sealing rotatable engagement with each other,
   a swivel tube mounted to said handpiece connector portion and rotatably mating in sealing engagement within said hose connector portion, said swivel tube including an outer cylindrical casing, an inner concentric cylindrical casing, and a spacer member separating said inner and outer casings and defining therewith a plurality of arcuate longitudinal passages including a drive air passage, a secondary air passage, and a water passage,
   said inner casing containing an optical fiber light guide in optical communication with the optical fiber light conduit in said hose,
   said drive air passage adapted for communication at one end thereof with said drive air conduit in said hose, and at the other end thereof with said drive air conduit in said handpiece,
   said secondary air passage being closed at its ends and communicating through radial ports inward thereof with secondary air annuli in respectively said hose connector portion and said handpiece connector portion of said coupling, said secondary air annuli in turn adapted for communication respectively with said secondary air conduits in said hose and said handpiece,
   said water passage being closed at its ends and communicating through radial ports inward thereof with water annuli in respectively said hose connector portion and said handpiece connector portion of said coupling, said water annuli in turn adapted for communication respectively with said water conduits in said hose and said handpiece,
   whereby said swivel coupling provides for the transmission therethrough of drive air, secondary air, water and light with unlimited swivel capability and with maximum use of space within said swivel tube.

* * * * *